US012728295B2

(12) United States Patent
Nemoto et al.

(10) Patent No.: US 12,728,295 B2
(45) Date of Patent: Sep. 8, 2026

(54) ULTRASONIC THERAPEUTIC DEVICE

(71) Applicant: SONIRE THERAPEUTICS INC., Tokyo (JP)

(72) Inventors: Kazuhito Nemoto, Tokyo (JP); Tsuyoshi Ueyama, Tokyo (JP)

(73) Assignee: SONIRE THERAPEUTICS INC., Tokyo (JP)

( * ) Notice: Subject to any disclaimer, the term of this patent is extended or adjusted under 35 U.S.C. 154(b) by 0 days.

(21) Appl. No.: 18/706,743

(22) PCT Filed: Mar. 10, 2022

(86) PCT No.: PCT/JP2022/010587
§ 371 (c)(1),
(2) Date: May 2, 2024

(87) PCT Pub. No.: WO2023/095355
PCT Pub. Date: Jun. 1, 2023

(65) Prior Publication Data

US 2025/0018229 A1 Jan. 16, 2025

(30) Foreign Application Priority Data

Nov. 29, 2021 (JP) ................................ 2021-192735

(51) Int. Cl.
*A61N 7/02* (2006.01)
*A61N 7/00* (2006.01)

(52) U.S. Cl.
CPC ........ *A61N 7/02* (2013.01); *A61N 2007/0052* (2013.01)

(58) Field of Classification Search
CPC ....................................................... A61N 7/02
See application file for complete search history.

(56) References Cited

U.S. PATENT DOCUMENTS 6,375,618 B1 * 4/2002 Chiao ..................... A61B 8/13 600/447
2007/0078326 A1 4/2007 Yoshikawa et al.
(Continued)

FOREIGN PATENT DOCUMENTS

CN 109431536 A 3/2019
EP 1726261 A1 11/2006
(Continued)

OTHER PUBLICATIONS

Machine translation of JP 2013055984, Mar. 28, 2013.*
(Continued)

*Primary Examiner* — Carolyn A Pehlke
(74) *Attorney, Agent, or Firm* — ICE MILLER LLP; Justin D. Swindells

(57) ABSTRACT

The purpose of the present invention is to facilitate confirmation that an affected part has been accurately irradiated with therapeutic ultrasonic waves in therapy using an ultrasonic therapeutic device. A control unit executes a therapeutic ultrasonic wave transmission process, an irradiation region image generation process, and a B-mode image generation process. The therapeutic ultrasonic wave transmission process causes an ultrasonic vibrator to transmit therapeutic ultrasonic waves. The irradiation region image generation process causes an ultrasonic probe to transmit a plurality of ultrasonic waves at different timings, synthesizes a plurality of received signals based on the plurality of ultrasonic waves that are reflected by biological tissue and received by the ultrasonic probe, and generates irradiation region data based on harmonic components of the received signals. The B-mode image generation process uses any one of the plurality of received signals to generate B-mode image data of the biological tissue.

10 Claims, 5 Drawing Sheets

(56) References Cited

U.S. PATENT DOCUMENTS

| | | | |
|---|---|---|---|
| 2008/0228076 A1 | 9/2008 | Azuma et al. | |
| 2010/0317971 A1 | 12/2010 | Fan et al. | |
| 2011/0009734 A1* | 1/2011 | Foley | A61N 7/02 601/2 |
| 2013/0274608 A1 | 10/2013 | Takeda et al. | |
| 2013/0296743 A1* | 11/2013 | Lee | G16H 50/30 601/3 |
| 2018/0169444 A1 | 6/2018 | Averkiou et al. | |
| 2020/0269074 A1* | 8/2020 | Inada | A61B 8/54 |
| 2021/0212709 A1 | 7/2021 | Pernot et al. | |

FOREIGN PATENT DOCUMENTS

| | | | | |
|---|---|---|---|---|
| EP | 1757244 | A1 | | 2/2007 |
| JP | H05-300909 | A | | 11/1993 |
| JP | H08-071069 | A | | 3/1996 |
| JP | 2004-344672 | A | | 12/2004 |
| JP | 2004344672 | | | 12/2004 |
| JP | 2013-055984 | A | | 3/2013 |
| JP | 2013-192627 | A | | 9/2013 |
| JP | 2014233305 | A | * | 12/2014 |
| JP | 2019-150361 | A | | 9/2019 |
| WO | 2005/058168 | A2 | | 6/2005 |
| WO | 2005/087109 | A1 | | 9/2005 |
| WO | 2019/224350 | A1 | | 11/2019 |
| WO | 2020167640 | A1 | | 8/2020 |

OTHER PUBLICATIONS

Izadifar, Zahra, et al. "An introduction to high intensity focused ultrasound: systematic review on principles, devices, and clinical applications." Journal of clinical medicine 9.2 (2020): 460.*

Rivens, I., et al. "Treatment monitoring and thermometry for therapeutic focused ultrasound." International journal of hyperthermia 23.2 (2007): 121-139.*

Office Action in parent Japanese application No. 2021-192735, Apr. 12, 2022, with machine translation (11 pages).

International Search Report in parent application No. PCT/JP2022/010587, with English translation, May 24, 2022 (4 pages).

Extended European Search Report issued in corresponding Europe Application No. 22896853.3 mailed Oct. 28, 2025.

* cited by examiner

ULTRASONIC THERAPEUTIC DEVICE

CROSS-REFERENCE TO RELATED APPLICATIONS

This application is a National Stage of International Application No. PCT/JP2022/010587 filed Mar. 10, 2022, which claims priority to Japan Patent Application No. 2021-192735 filed Nov. 29, 2021, the disclosures of which are incorporated herein by reference in their entirety.

TECHNICAL FIELD

The present invention relates to an ultrasonic therapeutic apparatus, and more particularly to an apparatus including an ultrasonic transducer for treatment and an ultrasonic probe for image generation.

BACKGROUND

Therapeutic apparatuses to which high-intensity focused ultrasound therapy is adopted are widely used. Such a therapeutic apparatus is referred to as a high-intensity focused ultrasound (HIFU) irradiation apparatus or a HIFU irradiation system, which irradiates a site to be treated with ultrasonic waves to destroy tissues.

A HIFU irradiation apparatus typically includes a plurality of ultrasonic transducers disposed on a semi-sphere or bowl face. The plurality of ultrasonic transducers are disposed to allow ultrasonic waves emanating from the respective ultrasonic transducers to be focused on a single point to form a focal point. During treatment, the focal point is aligned with a site to be treated, which is then irradiated with ultrasonic waves. The irradiated location is confirmed using an ultrasonic diagnosis device that indicates the focal point on an ultrasonic image.

Patent Document 1 listed below discloses an ultrasonic therapeutic apparatus that observes the location of a focal point using an ultrasonic diagnosis device that displays a B-mode image (tomographic image). This apparatus emits from therapeutic ultrasonic transducers ultrasonic waves of weak level that do not affect tissue, and transmits and receives ultrasonic waves with an ultrasonic imaging probe to display a tomographic image. Acoustic properties of tissue of a test subject change with the temperature of the tissue; therefore, the tomographic image indicates the location of a focal point with different levels of brightness.

Patent Document 2 listed below discloses, as a technology related to the invention of the present application, a technology for distinguishing echo components generated, by scattering, in a microbubble contrast medium, from components produced by nonlinear propagation of transmitted pulses.

CITATION LIST

Patent Literature

Patent Document 1: JP H8-71069 A

Patent Document 2: WO 2005/087109

SUMMARY

Technical Problem

In a treatment using a conventional HIFU irradiation apparatus, irradiation of an affected area with therapeutic ultrasound is confirmed based on both observation of locations of bubbles formed by the therapeutic ultrasound and observation of body tissue of a patient. The locations of bubbles are observed, for example, using harmonic imaging by transmitting ultrasonic waves from an ultrasonic probe toward the affected area and receiving harmonics generated from around the bubbles with the ultrasonic probe. The body tissue of the patient is observed based on a B-mode image acquired by transmission and reception of ultrasonic waves with the ultrasonic probe. This confirmation method, however, requires separate observations of the locations of bubbles and the body tissue, making the procedure complicated.

The present invention is aimed at facilitating confirmation that an affected area has been irradiated with therapeutic ultrasound in a treatment performed with an ultrasonic therapeutic apparatus.

Solution to Problem

The present invention includes an ultrasonic transducer for treatment, an ultrasonic probe, and a control unit configured to control the ultrasonic transducer and the ultrasonic probe. The control unit is configured to execute therapeutic ultrasound transmitting processing for causing the ultrasonic transducer to transmit therapeutic ultrasonic waves, irradiated-region image generating processing for causing the ultrasonic probe to transmit a plurality of ultrasonic waves at different times and combining a plurality of received signals based on the plurality of ultrasonic waves reflected by body tissue and received by the ultrasonic probe to generate irradiated-region data based on harmonic components based on the respective received signals, and B-mode image generating processing for generating B-mode image data of the body tissue by using one of the plurality of received signals.

Preferably, the control unit is configured to cause the display device to display a first image based on the irradiated-region data and a second image based on the B-mode image data.

Preferably, the control unit is configured to cause the display device to display the first image and the second image in a superimposed manner.

Preferably, the control unit is configured to display a figure representing a treatment reference region or a treatment reference point in accordance with a location of the ultrasonic transducer, in a superimposed manner on the second image.

Preferably, the control unit is configured to detect a movement of the body tissue based on the B-mode image data sequentially generated over time, and determine an amount of treatment at each of locations in a patient coordinate system fixed to the body tissue, based on each of the irradiated region data corresponding to the respective B-mode image data.

Preferably, a drive device configured to drive the ultrasonic transducer is further provided, and the control unit is configured to detect a movement of the body tissue based on the B-mode image data sequentially generated over time, and control the drive device in accordance with a movement of the body tissue to move the ultrasonic transducer in accordance with the movement of the body tissue.

Advantageous Effects

The present invention facilitates confirmation that an affected area has been irradiated with therapeutic ultrasound.

DESCRIPTION OF EMBODIMENTS

Figure 1:
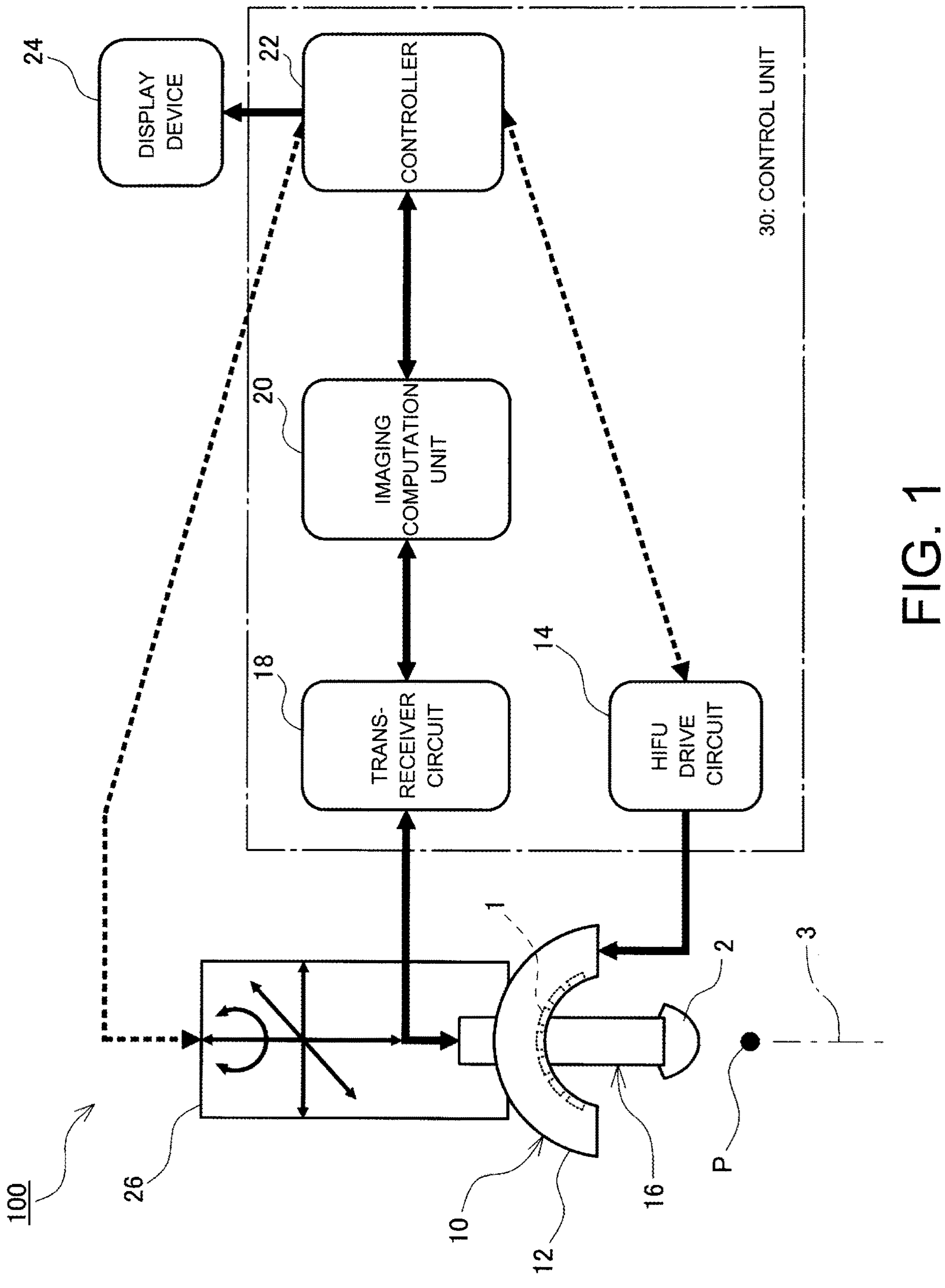
FIG. 1 illustrates a HIFU irradiation apparatus.

An embodiment of the present invention will be described by reference to the drawings. In the drawings, identical elements are denoted with identical reference numerals and their descriptions are not repeated. FIG. 1 illustrates a configuration of a HIFU irradiation apparatus 100 (ultrasonic therapeutic apparatus) according to an embodiment of the present invention. The HIFU irradiation apparatus 100 includes a HIFU transducer unit 10, a HIFU drive circuit 14, an ultrasonic probe 16, a transreceiver circuit 18, an imaging computation unit 20, a controller 22, a display device 24, and a drive device 26.

The controller 22 may be a personal computer or a tablet computer, for example. An operation device (not shown) that allows a user to operate the HIFU irradiation apparatus 100 is connected to the controller 22. The operation device may include a mouse, a touch panel integrated with the display device 24, a switch, and a keyboard, for example.

The HIFU transducer unit 10 includes a semi-sphere bowl shape transducer housing 12 opened downward, and a plurality of ultrasonic transducers 1 secured to the transducer housing 12. The transducer housing 12 may have a shape similar to a shape of a cone. The cone as used herein refers to a three-dimensional shape formed of a set of straight lines extending from one point within a space to a bottom face. The ultrasonic transducers 1 are secured to the transducer housing 12 in such a manner that ultrasonic waves emitted from the respective ultrasonic transducers 1 have an increased intensity at a treatment reference point P beneath the transducer housing 12.

The HIFU drive circuit 14 causes each ultrasonic transducer 1 of the HIFU transducer unit 10 to generate ultrasonic waves under control of the controller 22. The HIFU drive circuit 14 further adjusts the intensity of the ultrasonic waves emitted from each ultrasonic transducer 1.

The ultrasonic probe 16 is secured to the transducer housing 12 to transmit and receive ultrasonic waves at a location below the transducer housing 12 and above the treatment reference point P. In this embodiment, the ultrasonic probe 16 extends vertically through the top of the transducer housing 12, with a transreceiver unit 2 that transmits and receives the ultrasonic waves, facing downward.

The transreceiver circuit 18 and the imaging computation unit 20 may be a typical ultrasonic diagnostic device. The imaging computation unit 20 may be composed of a processor that executes a program to control the transreceiver circuit 18. The transreceiver circuit 18 executes the following processing under control of the imaging computation unit 20. Specifically, the transreceiver circuit 18 causes the ultrasonic probe 16 to transmit ultrasonic waves to scan a beam based on the transmitted ultrasonic waves (ultrasound beam). The ultrasound beam is scanned with an observation face including a center axis 3 extending vertically from the top of the transducer housing 12. The transreceiver circuit 18 further causes the ultrasonic probe 16 to receive reflected ultrasonic waves from a direction in which the ultrasound beam is directed, and acquires, from the ultrasonic probe 16, received signals based on reflected ultrasonic waves received from each direction in which the ultrasound beam is directed. The transreceiver circuit 18 outputs each received signal to the imaging computation unit 20.

The imaging computation unit 20 generates ultrasound data based on each received signal output from the transreceiver circuit 18. The ultrasound data may be irradiated-region data representing a region of body tissue of a patient where harmonic components are generated, or B-mode image data representing a B-mode image (tomographic image) acquired with regard to body tissue of a patient.

The drive device 26 moves the HIFU transducer unit 10 and the ultrasonic probe 16 under control of the controller 22 to adjust the positions of the HIFU transducer unit 10 and the ultrasonic probe 16. The drive device 26, under control of the controller 22, may rotate the ultrasonic probe 16 about the center axis 3 to rotate the observation face of the ultrasonic probe 16 about the center axis 3.

Prior to irradiating of the patient with therapeutic ultrasound from the HIFU transducer unit 10, positioning as described below is executed. The HIFU drive circuit 14 causes each of the ultrasonic transducers 1 to transmit ultrasonic waves of an intensity that is smaller than the intensity of the ultrasonic waves applied during treatment. The drive device 26 sets the rotation angle position of the ultrasonic probe 16 to allow the ultrasonic probe 16 to scan the ultrasound beam with the observation face at a predetermined rotation angle position.

The imaging computation unit 20 causes the ultrasonic probe 16 to scan the ultrasound beam with the observation face, acquires the B-mode image data or the ultrasound data, and outputs the B-mode image data to the controller 22. The controller 22 causes the display device 24 to display the B-mode image. The user or practitioner references to the B-mode image displayed on the display device 24 to confirm a difference between the location where the intensity of the ultrasonic waves transmitted from the HIFU transducer unit 10 is increased (focal point) and the location of the affected area.

When the difference between the location of the focal point and the location of the affected area is not within the allowable range, the user changes the locations or positions of the ultrasonic probe 16 and the HIFU transducer unit 10. After confirming that the location of the focal point and the location of the affected area match or that the difference between the location of the focal point and the location of the affected area falls within the allowable range, the user operates the controller 22 for treatment. The controller 22 controls the HIFU drive circuit 14 in accordance with the user operation. The HIFU drive circuit 14 causes each ultrasonic transducer 1 to transmit therapeutic ultrasound having an intensity required for the treatment under control of the controller 22. This achieves cauterization of the body tissue at the focal point for treatment.

Figure 2:
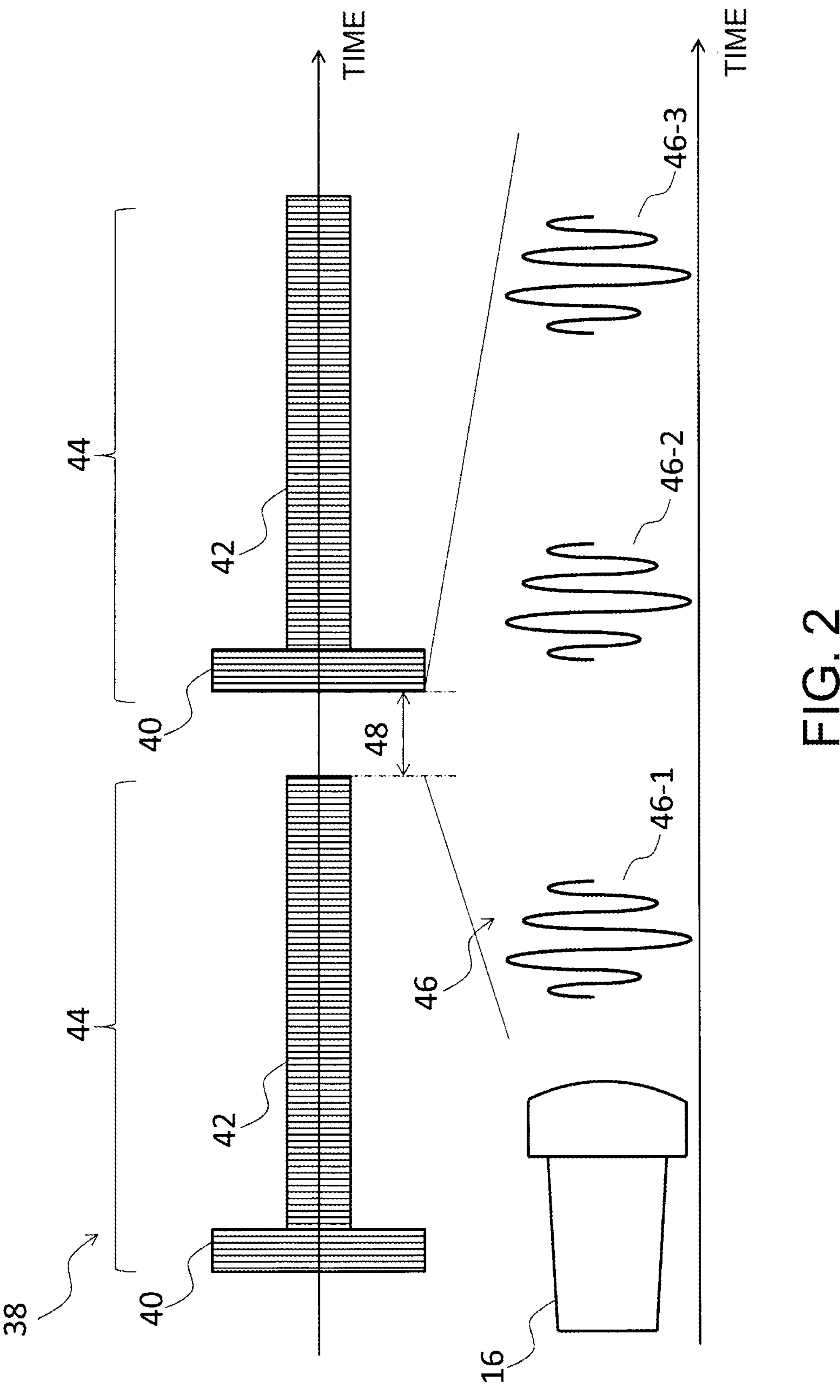
FIG. 2 conceptually shows time waveforms of therapeutic ultrasound and imaging ultrasound.

The HIFU irradiation apparatus 100 executes, while irradiating the patient with therapeutic ultrasound, irradiated-region display processing for displaying an image representing an irradiated region that is irradiated with the therapeutic ultrasound, on the display device 24, in a superimposed manner on the B-mode image. Here, the processing for displaying the two images in a superimposed manner may be processing for generating new image data by combining the image data to enable one image to be seen through the other image, and displaying an image based on the new image data. FIG. 2 conceptually illustrates time waveforms of therapeutic ultrasound 38 transmitted from the HIFU transducer unit 10 and imaging ultrasound 46 transmitted from the ultrasonic probe 16 during execution of the irradiated-region display processing.

The therapeutic ultrasound 38 comprises strong-and-weak ultrasonic pulses 44 including strong-level ultrasound 40 and weak-level ultrasound 42 following the strong-level ultrasound 40. The strong-and-weak ultrasonic pulses 44 are transmitted repeatedly from the HIFU transducer unit 10 over time. An irradiation pause period 48 is provided between two strong-and-weak ultrasonic pulses 44 adjacent each other on a time axis, and transmission of the therapeutic ultrasound 38 is interrupted during the irradiation pause period 48.

Transmission of the strong-and-weak ultrasonic pulses 44 from the HIFU transducer unit 10 causes cauterization of body tissue at the focal point. The body tissue, when irradiated with the strong-level ultrasound 40, generates bubbles, and the state in which bubbles are generated is maintained by irradiation with the weak-level ultrasound 42.

During the irradiation pause period 48, the imaging ultrasonic waves 46 for generating the ultrasound data are transmitted three times from the ultrasonic probe 16. A second imaging ultrasonic wave 46-2 transmitted at the second time is delayed by a phase of 120° with respect to a first imaging ultrasonic wave 46-1 transmitted at the first time, and a third imaging ultrasonic wave 46-3 transmitted at the third time is delayed by a phase of 120° with respect to the second imaging ultrasonic wave 46-2.

Each imaging ultrasonic wave 46 is reflected within the body tissue. Reflection of each imaging ultrasonic wave 46 around the bubbles caused by the strong-and-weak ultrasonic pulses 44 causes generation of harmonics. Reflected ultrasonic waves from the body tissue therefore contain the harmonics caused by the bubbles, in addition to fundamental waves. Typically, the greater the amount of bubbles formed, the greater the intensity of harmonics generated.

Returning to FIG. 1, processing for receiving reflected waves in response to the respective imaging ultrasonic waves 46 by the HIFU irradiation apparatus 100 will be described. The ultrasonic probe 16 receives first to third imaging ultrasonic waves in response to the first imaging ultrasonic wave 46-1 to the third imaging ultrasonic wave 46-3, and outputs first to third received signals to the transreceiver circuit 18. The transreceiver circuit 18 performs amplification, for example, on the first to third received signals, and outputs the resulting signals to the imaging computation unit 20.

The imaging computation unit 20 sums up the first received signal, the second received signal, and the third received signal, to generate a harmonic signal containing a sum of harmonic components included in the first to third received signals. In the signals obtained by summing the first to third received signals, the fundamental wave components are reduced due to the phase relation of the first imaging ultrasonic wave 46-1 to the third imaging ultrasonic wave 46-3. The imaging computation unit 20 generates the harmonic signal with respect to the first to third reflected ultrasonic waves coming from each direction to which the ultrasonic beam is directed, and generates irradiated-region data based on the harmonic signals generated for the respective directions. The irradiated-region data are image data representing an irradiated region image indicating a region where the bubbles are formed, in a region in which the ultrasound beams are scanned.

The imaging computation unit 20 further generates a B-mode image based on one of the first reflected ultrasonic wave to the third reflected ultrasonic wave. For example, the imaging computation unit 20 generates, based on the second reflected ultrasonic wave coming from each direction to which the ultrasonic beam is directed, pixel data of the B-mode image for each direction, and generates B-mode image data based on the pixel data acquired for each direction. The reflected ultrasonic wave serving as a source of the B-mode image data may be the first reflected ultrasonic wave or the third reflected ultrasonic wave.

The imaging computation unit 20 outputs the irradiated-region data and the B-mode image data to the controller 22. The controller 22, based on the irradiated-region data and the B-mode image data, causes the display device 24 to display an image including the B-mode image superimposed on the irradiated region image (B-mode irradiated-region image).

The imaging computation unit 20 outputs the irradiated-region data and the B-mode image data at a frame time interval (the inverse of a frame rate) to the controller 22. The controller 22 causes the display device 24 to sequentially display the B-mode irradiated-region images over time. The controller 22 may cause the display device 24 to display a figure indicating the treatment reference point P in a superimposed manner on the B-mode irradiated region image. The controller 22 may also cause the display device 24 to display a figure indicating a region in the vicinity of the treatment reference point P and the treatment reference point P (treatment reference region) in a superimposed manner on the B-mode irradiated region image.

The controller 22 may display the image based on the irradiated region data and the B-mode image individually, rather than in a superimposed manner. For example, the controller 22 may cause the display device 24 to display the image based on the irradiated-region data and the B-mode image such that these images are arranged in a comparable manner.

Figure 3:
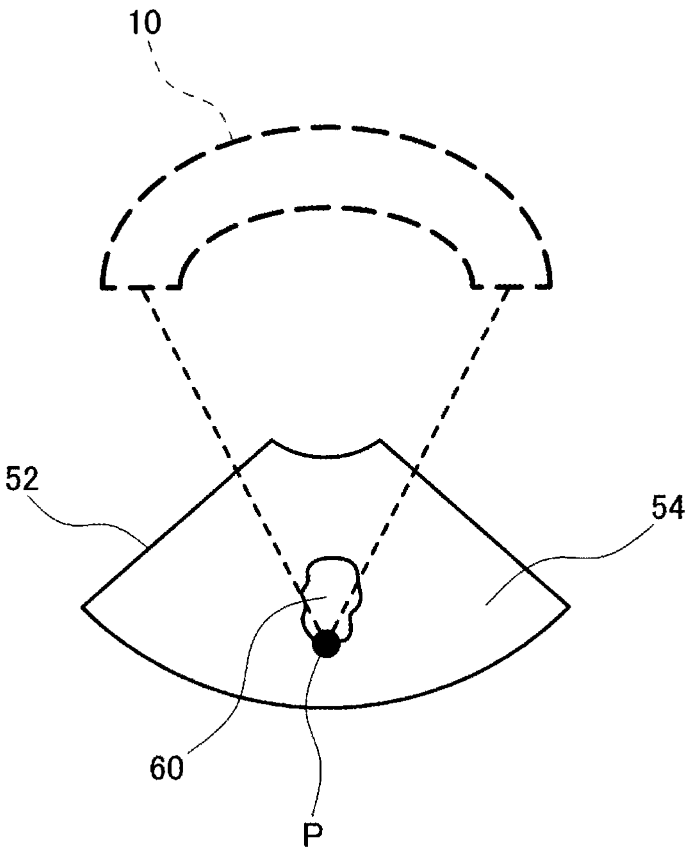
FIG. 3 schematically illustrates a B-mode irradiated region image, along with a HIFU transducer unit.

FIG. 3 schematically illustrates a B-mode irradiated-region image 52 along with the HIFU transducer unit 10. A B-mode image 54 is displayed within a scanning region in which the ultrasound beams are scanned, and an image of a bubble generated by harmonics of reflected waves is shown as an irradiated region 60.

While in the above description, the imaging ultrasonic waves for generating ultrasound data are transmitted three times, the imaging ultrasonic waves may be transmitted twice, or four or more times. When transmitting the imaging ultrasonic waves M times, the phase difference between adjacent imaging ultrasonic waves on the time axis is 360°/M. Alternatively, the phases of the imaging ultrasonic waves may be set such that the phase of $\theta+i\cdot 360°/M$ ($\theta$ is any phase, and i is an integer of 0 to $M-1$) is assigned to each of the M imaging ultrasonic waves, independently of the order of transmission.

The imaging computation unit 20 sums up the first received signal to the M-th received signal to generate a harmonic signal containing a sum of harmonic components contained in the first to M-th received signals. The imaging computation unit 20 further generates a B-mode image based on one of the first to M-th reflected ultrasonic waves.

As described above, the HIFU irradiation apparatus 100 includes the HIFU transducer unit 10 including the ultrasonic transducers 1 for treatment, the ultrasonic probe 16, and a control unit 30 that controls the ultrasonic transducers 1 and the ultrasonic probe 16. The control unit 30 is composed of the HIFU drive circuit 14, the transreceiver circuit 18, the imaging computation unit 20, and the controller 22.

The control unit 30 executes therapeutic ultrasound transmitting processing, irradiated-region image generating processing, and B-mode image generating processing. The therapeutic ultrasound transmitting processing is executed to cause the ultrasonic transducers 1 to transmit therapeutic ultrasound. The irradiated-region image generating processing is executed to cause the ultrasonic probe 16 to transmit a plurality of ultrasonic waves at different times, sum or combine the first to M-th received signals (a plurality of received signals) based on the first to M-th reflected ultrasonic waves (a plurality of ultrasonic waves) that have been reflected on body tissue and then received by the ultrasonic probe 16, and generate irradiated-region data based on harmonic components of the respective received signals. The B-mode image generating processing is executed to generate B-mode mage data of body tissue with any one of the received signals.

The control unit 30 executes display processing to cause the display device 24 to display a first image based on the irradiated-region data and a second image based on the B-mode image data. The control unit 30 may cause the display device 24 to display the first image and the second image in a superimposed manner. The control unit 30 may further cause the display device 24 to display a figure representing the treatment reference region in accordance with the location of the ultrasonic transducer 1 or a figure representing the treatment reference point P in a superimposed manner on the second image.

These configuration and processing enable irradiation of the body tissue with the therapeutic ultrasound and display of a region irradiated with the therapeutic ultrasound on the B-mode image. The B-mode image data are generated with the use of reflected ultrasonic waves based on any one of a plurality of imaging ultrasonic waves for use in generating the irradiated-region data. This enables the user to easily confirm that the affected area has been irradiated with the therapeutic ultrasound.

The controller 22 (control unit 30) may determine patient coordinate system irradiation data representing irradiation amounts correlated to corresponding coordinate values, respectively, in a patient coordinate system fixed to a patient (locations in the patient coordinate system fixed to body tissue). The irradiation amount may be defined as a pixel value of the irradiated region. The patient coordinate system irradiation data represent a distribution of the irradiation amounts in the patient coordinate system. The controller 22 executes tracking processing with respect to the B-mode image data sequentially output from the imaging computation unit 20 at frame time intervals to detect the movement of the body tissue appearing in the B-mode image, on the B-mode image. The detection may be performed as follows.

The controller 22, based on the B-mode image data, generates data that specify the contour of the body tissue. The controller 22 determines, with respect to the respective coordinate values in the patient coordinate system fixed for this contour, the irradiation amounts, based on pixel values of the irradiated-region data acquired along with the B-mode image data, to thereby generate the patient coordinate system irradiation data. Generation of the patient coordinate system irradiation data for each set of B-mode image data sequentially output from the imaging computation unit 20 at frame time intervals results in generation of the patient coordinate irradiation data that track the movement of the body tissue on the B-mode image.

Figure 4:
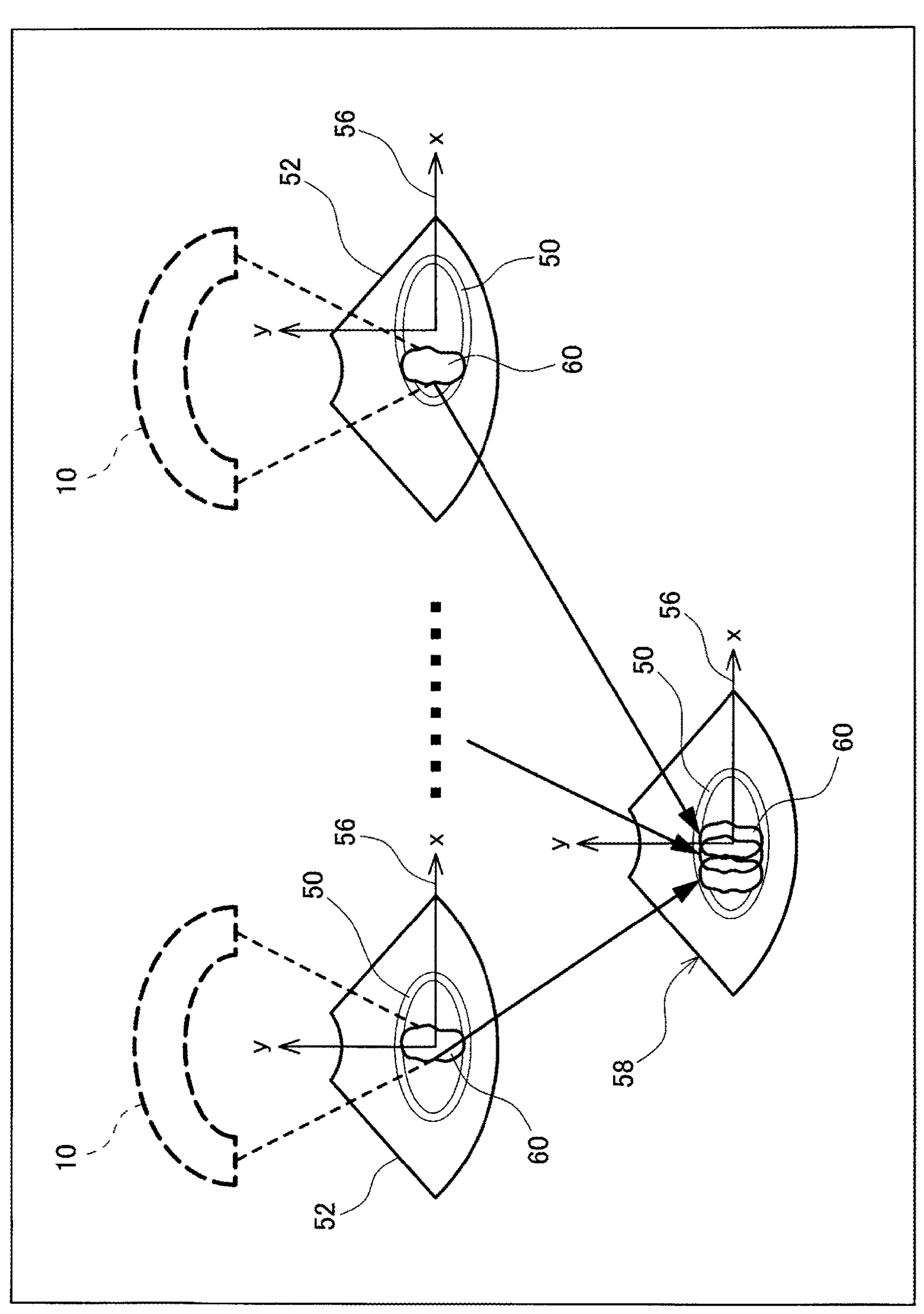
FIG. 4 illustrates B-mode irradiated region images that change over time, and a treatment amount distribution.

FIG. 4 illustrates, in the upper portion, the B-mode irradiated region images 52 sequentially generated over time, along with xy coordinates or a patient coordinate system 56. The B-mode irradiated-region image 52 changes over time, from the image shown on the left side to the image shown on the right side. In the example illustrated in the upper portion in FIG. 4, the patient moves to the right, and the contour of the body tissue 50 and the patient coordinate system 56 move to the right over time. The irradiated region 60 does not move relative to the B-mode irradiated-region image 52, but moves to the left relative to the patient coordinate system 56. The patient coordinate system irradiation data represent the irradiation amounts for the respective coordinate values of the patient coordinate system 56 that moves to the right with the patient.

The controller 22 may determine the patient coordinate system irradiation data for each set of B-mode image data sequentially output from the imaging computation unit 20 at frame time intervals, to determine the treatment amount by summing the irradiation amounts for a predetermined number of frames, for each of the coordinate values in the patient coordinate system. The controller 22 may determine treatment amount distribution data representing the treatment amounts related to the respective coordinate values in the patient coordinate system.

FIG. 4 illustrates, in the lower portion, a treatment amount distribution 58 represented by the treatment amount distribution data generated for the patient coordinate system 56. The treatment amount obtained by summing the pixel values in the irradiated region 60 at each time is represented by a figure including the irradiated regions 60 superimposed at each time. The treatment amount distribution 58 shows that the movement of the patient results in the treatment amounts distributed in the left part of the contour 50.

The controller 22 may cause the display device 24 to display a treatment amount distribution image based on the treatment amount distribution data. The treatment amount distribution image refers to an image that represents the distribution of the treatment amounts in the patient coordinate system. The controller 22 may further cause the display device 24 to display a treatment amount distribution image indicating pixels that represent body tissue with a greater brightness as the treatment amount increases. Alternatively, the treatment amount distribution image may have a color in accordance with the treatment amount.

As described above, the controller 22 detects the movement of body tissue based on the B-mode image data sequentially generated over time, and obtains the treatment amount at each location in the patient coordinate system fixed to the body tissue based on each irradiated-region data corresponding to each set of B-mode image data. The treatment amount distribution data refers to data representing the treatment amount correlated to each location in the patient coordinate system fixed to the body tissue. Therefore, the treatment amount correlated to the body tissue of a patient can be indicated even when the patient moves during treatment.

Tracking irradiation processing according to an applied embodiment of the present invention will be described. This processing is performed, in response to the movement of a patient, to move the HIFU transducer unit 10 and the ultrasonic probe 16 to allow the treatment reference point P to track the movement of the body tissue for emitting the therapeutic ultrasound. During the tracking irradiation processing, the controller 22 (control unit 30), based on the B-mode image data sequentially generated over time, detects the movement of body tissue and controls the drive device 26 in accordance with the movement of the body tissue to move the ultrasonic transducers 1 of the HIFU transducer unit 10 in accordance with the movement of the body tissue.

The controller 22 executes tracking processing with respect to the B-mode image data sequentially output from the imaging computation unit 20 at the frame time intervals. Specifically, the controller 22 determines an amount of displacement, on a B-mode image, of the body tissue appearing on the B-mode image, at the frame time intervals. For example, the controller 22, based on the B-mode image data, generates data that specify the contour of body tissue, and, based on each set of B-mode image data generated at data frame time intervals, determines the amount of displacement of the contour at the frame time intervals. The controller 22 controls the drive device 26 such that the treatment reference point P moves by the amount of displacement of the contour at time intervals that are K times the frame time intervals, where K is an integer that is 1 or greater. The drive device 26 moves the HIFU transducer unit 10 and the ultrasonic probe 16 under control of the controller 22.

Figure 5:
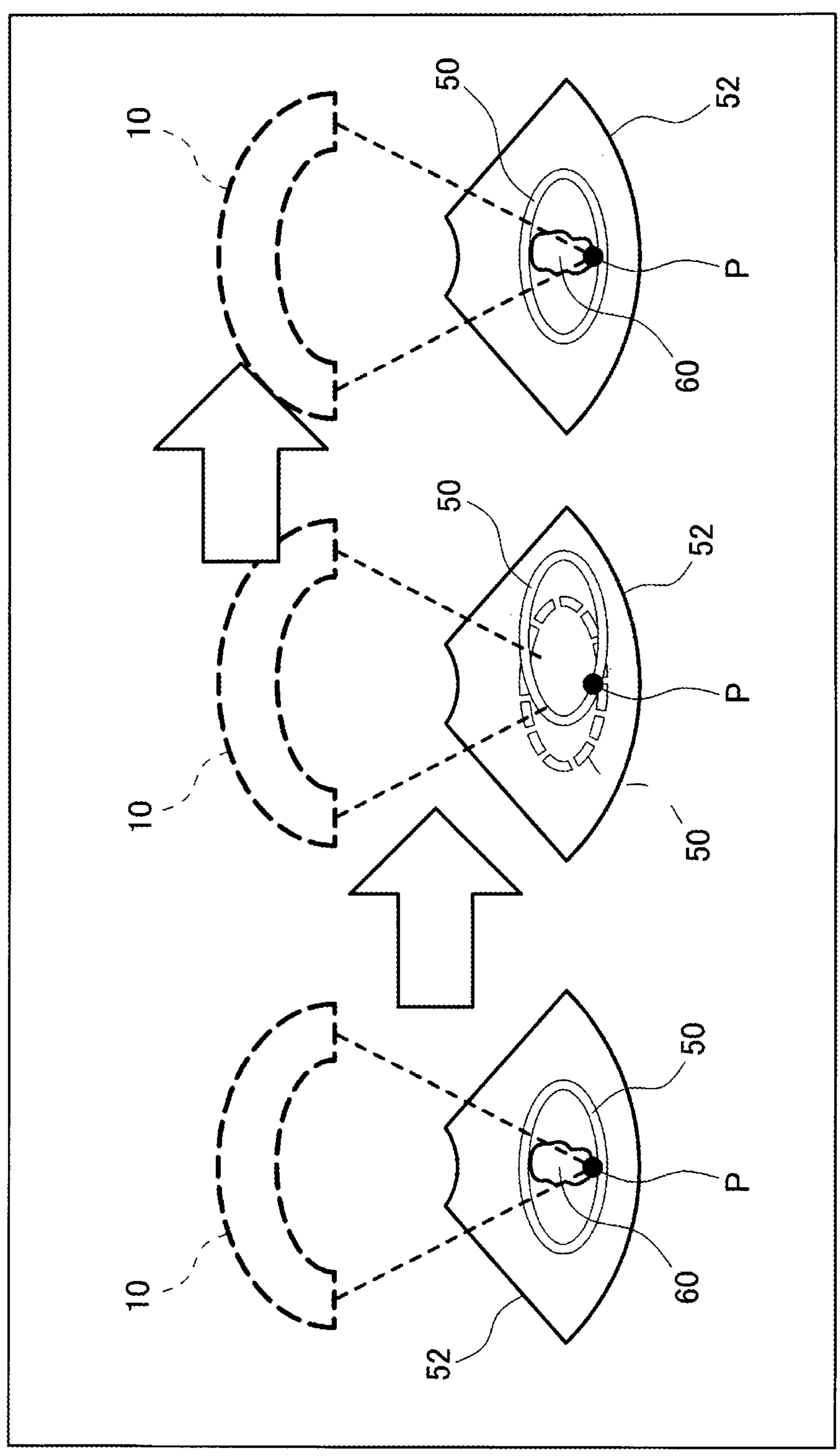
FIG. 5 schematically illustrates a B-mode irradiated region image under tracking irradiation processing, a contour of body tissue, and a HIFU transducer unit.

FIG. 5 schematically illustrates the B-mode irradiated-region image 52, the body tissue contour 50, and the HIFU transducer unit 10 under the tracking irradiation processing. As illustrated in the left figure in FIG. 5, the B-mode irradiated-region image 52 shows the irradiated region 60 as a bubble image (an image by harmonic imaging), and the body tissue contour 50. As illustrated in the left figure in FIG. 5, the irradiated region 60 is located within the contour 50. The center figure in FIG. 5 shows that a movement of the patient's body to the right causes the contour 50 to move rightward from the original position indicated with a dashed line. The right figure in FIG. 5 shows that the HIFU transducer unit 10 moves to the right following the movement of the contour 50. The irradiated region 60 is located back to the vicinity of the center of the body tissue contour 50, which shows irradiation of the therapeutic ultrasound at a proper location. While FIG. 5 indicates the contour 50 on the B-mode irradiated-region image 52, the contour 50 need not be displayed on the display device 24.

This configuration and this processing allow the focal point of the therapeutic ultrasound to track the movement of the contour 50 or the movement of specific body tissue in accordance with the movement of the patient during treatment. This enables the focal point to track the movement of an affected area in accordance with the movement of the patient's body, thereby allowing the affected area to be irradiated with the therapeutic ultrasound.

REFERENCE SIGNS LIST

10 HIFU transducer unit, 12 ultrasonic transducer, 14 HIFU drive circuit, 16 ultrasonic probe, 18 transreceiver circuit, 20 imaging computation unit, 22 controller, 24 display device, 26 drive device, 40 strong-level ultrasound, 42 weak-level ultrasound, 44 strong and weak ultrasonic pulses, 46-1 first imaging ultrasonic wave, 46-2 second imaging ultrasonic wave, 46-3 third imaging ultrasonic wave, 48 irradiation pause period, 50 contour, 52 B-mode irradiated-region image, 54 B-mode image, 56 patient coordinate system, 58 treatment amount distribution, 60 irradiated region, 100 HIFU irradiation apparatus.

What is claimed is:

1. An ultrasonic therapeutic apparatus comprising:

at least one ultrasonic transducer for treatment based on high intensity focused ultrasound therapy;

an ultrasonic probe; and a controller configured to control the ultrasonic transducer and the ultrasonic probe, wherein the controller is configured to execute:

therapeutic ultrasound transmitting processing for causing the ultrasonic transducer to transmit therapeutic ultrasonic waves to a body tissue;

irradiated-region image generating processing for causing the ultrasonic probe to transmit a plurality of ultrasonic waves at different times and different phases, and combining a plurality of received signals based on the plurality of ultrasonic waves reflected by the body tissue and received by the ultrasonic probe to thereby generate irradiated-region data based on harmonic components based on the respective received signals, and B-mode image generating processing for generating B-mode image data of the body tissue by using one of the plurality of received signals received by the ultrasonic probe, and the controller is further configured to:

detect a movement of the body tissue based on the B-mode image data sequentially generated over time; and specify a patient coordinate system fixed to the body tissue based on the B-mode image data sequentially generated over time; and determine an amount of treatment at each of locations in the patient coordinate system fixed to the body tissue, based on each of the irradiated region data corresponding to the respective B-mode image data, the amount of treatment being based on a pixel value of the irradiated region data at each of the locations in the patient coordinate system.

2. The ultrasonic therapeutic apparatus according to claim 1, wherein the controller is configured to:

cause the display device to display a first image based on the irradiated-region data and a second image based on the B-mode image data.

3. The ultrasonic therapeutic apparatus according to claim 2, wherein the controller is configured to:

cause the display device to display the first image and the second image in a superimposed manner.

4. The ultrasonic therapeutic apparatus according to claim 2, wherein the controller is configured to:

display a figure representing a treatment reference region or a treatment reference point in accordance with a location of the ultrasonic transducer, in a superimposed manner on the second image.

5. The ultrasonic therapeutic apparatus according to claim 1, wherein the at least one ultrasound transducer comprises a plurality of ultrasonic transducers disposed on a semi-sphere face, the ultrasonic therapeutic apparatus comprising:

a drive device configured to drive move the plurality of ultrasonic transducers, wherein the controller is configured to:

detect a movement of the body tissue based on the B-mode image data sequentially generated over time; and control the drive device in accordance with a movement of the body tissue to move a focal point where an intensity of ultrasonic waves transmitted from the plurality of ultrasonic transducers is increased.

6. An ultrasonic therapeutic apparatus comprising:

at least one ultrasonic transducer for treatment based on high intensity focused ultrasound therapy;

an ultrasonic probe; and a controller configured to control the ultrasonic transducer and the ultrasonic probe, wherein the controller is configured to execute:

therapeutic ultrasound transmitting processing for causing the ultrasonic transducer to transmit therapeutic ultrasonic waves to a body tissue;

irradiated-region image generating processing for causing the ultrasonic probe to transmit a plurality of ultrasonic waves at different times and different phases, and combining a plurality of received signals based on the plurality of ultrasonic waves reflected by the body tissue and received by the ultrasonic probe to thereby generate irradiated-region data based on harmonic components based on the respective received signals, and B-mode image generating processing for generating B-mode image data of the body tissue by using one of the plurality of received signals received by the ultrasonic probe, wherein the controller is further configured to cause the display device to display a treatment amount distribution image based on a treatment amount determined from irradiation in the irradiated-region data, the treatment amount distribution image indicating pixels that represent body tissue with a greater brightness as the treatment amount increases, wherein the controller is further configured to:

detect a movement of the body tissue based on the B-mode image data sequentially generated over time;

specify a patient coordinate system fixed to the body tissue based on the B-mode image data sequentially generated over time; and determine the treatment amount at each of locations in the patient coordinate system fixed to the body tissue, based on each of the irradiated region data corresponding to the respective B-mode image data, the treatment amount being based on a pixel value of the irradiated region data at each of the locations in the patient coordinate system.

7. The ultrasonic therapeutic apparatus according to claim 6, wherein the controller is configured to:

cause the display device to display a first image based on the irradiated-region data and a second image based on the B-mode image data.

8. The ultrasonic therapeutic apparatus according to claim 7, wherein the controller is configured to:

cause the display device to display the first image and the second image in a superimposed manner.

9. The ultrasonic therapeutic apparatus according to claim 7, wherein the controller is configured to:

display a figure representing a treatment reference region or a treatment reference point in accordance with a location of the ultrasonic transducer, in a superimposed manner on the second image.

10. The ultrasonic therapeutic apparatus according to claim 6, wherein the at least one ultrasound transducer comprises a plurality of ultrasonic transducers disposed on a semi-sphere face, the ultrasonic therapeutic apparatus comprising:

a drive device configured to drive move the plurality of ultrasonic transducers, wherein the controller is configured to:

detect a movement of the body tissue based on the B-mode image data sequentially generated over time; and control the drive device in accordance with a movement of the body tissue to move a focal point where an intensity of ultrasonic waves transmitted from the plurality of ultrasonic transducers is increased.

* * * * *